(12) United States Patent
Shuber

(10) Patent No.: US 6,207,372 B1
(45) Date of Patent: *Mar. 27, 2001

(54) UNIVERSAL PRIMER SEQUENCE FOR MULTIPLEX DNA AMPLIFICATION

(75) Inventor: Anthony P. Shuber, Milford, MA (US)

(73) Assignee: Genzyme Corporation, Framingham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/983,466

(22) PCT Filed: Jun. 6, 1996

(86) PCT No.: PCT/US96/09637

§ 371 Date: Feb. 10, 1998

§ 102(e) Date: Feb. 10, 1998

(87) PCT Pub. No.: WO96/41012

PCT Pub. Date: Dec. 19, 1996

Related U.S. Application Data

(63) Continuation-in-part of application No. 08/474,450, filed on Jun. 7, 1995, now Pat. No. 5,882,856.

(51) Int. Cl.$^7$ .............................. C12Q 1/68; C12P 19/34; C07H 21/04
(52) U.S. Cl. ......................... 435/6; 435/91.1; 435/91.2; 536/24.3
(58) Field of Search ........................ 536/24.3; 435/91.2, 435/91.1, 6

(56) References Cited

U.S. PATENT DOCUMENTS

| | | |
|---|---|---|
| 5,104,792 | 4/1992 | Silver et al. ............................ 435/16 |
| 5,474,896 | * 12/1995 | Dujon et al. .............................. 435/6 |
| 5,518,901 | * 5/1996 | Murtagh .............................. 435/91.2 |
| 5,882,856 | * 3/1999 | Shuber ..................................... 435/6 |

FOREIGN PATENT DOCUMENTS

| | | | |
|---|---|---|---|
| 628640 | 12/1994 | (EP) ................................ | C12Q/1/68 |
| 89/12684 | * 12/1989 | (WO) ............................. | C12N/15/00 |
| WO 93/18177 | 9/1993 | (WO) ............................. | C12P/19/34 |
| WO 93/18178 | 9/1993 | (WO) ............................. | C12P/19/34 |

OTHER PUBLICATIONS

Edwards et al. Multiplex PCR: advantages, development, and applications, PCR Methods and Applications, vol. 3, pp. S65–S75, 1994.*
Berg et al. (1994) *Biotechniques*, 17(5):896–901.
Chenhui, T. (1993) *The Journal of Heredity*, 84(3):236–237.
Chetverin, A. (1994) *Bio/Technology*, 12:1093–1099.
Ebrahimi et al. (1992) *J. Chem. Soc. Chem. Commun.*, 1398–1399.
Edwards et al, (1994) *PCR Methods and Applications*, 3:565–575.
Feng et al. (1991) *Physical Review B*, 43(11):9284–9286.
Feng et al. (1992) "Modified Self–Consistent Phonon Calculation Of The Dependence Of DNA Melting Temperature On Guanine–Cytosine Content" 46(12):8002–8006.
Guatelli et al. (1989) *Clinical Microbiology Reviews*, 2(2):217–226.
Hung et al. (1990) *Nucleic Acids Research*, 18(16):4953.
Ide et al. (1995) *Nucleic Acids Research*, 23(1):123–129.
Jeffreys et al. (1991) *Nature*, 354:204–209.
Jones et al. (1991) *Bio/Technology*, 9:88–89.
Kumar et al. (1994) *Journal of Biomolecular Structure and Dynamics*, 12(1):183–201.
Melchior et al. (1973) *Proc. Nat. Acad. Sci. USA*, 70(2):298–302.
Moreau et al. (1994) *BioTechniques*, 17(2):233–234.
Morse et al. (1995) *Nucleic Acids Research*, 23(2):302–306.
Mutter et al. (1995) *Nucleic Acids Research*, 23(8):1411–1418.
Peral et al. (1994) *Am. J. Hum. Genet.*, 54:899–908.
Peyrard et al. (1992) *Nanobiology*, 1:313–324.
Picci et al. (1992) *Hum Genet.*, 88:552–556.
Ponnuswamy et al. (1994) *J. Theor. Biol.*, 169:419–432.
Record, Jr. et al. (1990) *Theoretical Biochemistry & Molecular Biophysics*, 28(4):285–307.
Orou et al. (1995) *TIG*, 11(4):127–128.
Rychlik, W. (1995) *BioTechniques*, 18(1):84–90.
Shuber et al. (1995) *Genome Research*, 5:488–498.
Sugimoto et al. (1991) *Agric. Biol. Chem.*, 55(11):2687–2692.
Sugimoto et al. (1995) *Biochemistry*, 34:11211–11216.
Sugimoto et al. (1993) *Analytical Biochemistry*, 211:170–172.
Tuliszka et al. (1992) *Thermochimica Acta*, 194:67–75.
Turner et al. (1995) *Biotechniques*, 19(1).
Wallace et al. (1979) *Nucleic Acids Research*, 6(11):3543–3557.
Weighardt et al. (1993) *PCR Methods and Applications*, 3:77–80.
Varanasi et al. (1994) *Proc. Nat. Acad. Sci. USA*, 91:3554–3558.

* cited by examiner

Primary Examiner—W. Gary Jones
Assistant Examiner—Joyce Tung

(57) ABSTRACT

The present invention provides primer that allow simultaneous amplification of multiple DNA target sequences present in a DNA sample. Further provided are methods for detecting multiple defined target DNA sequences in a DNA sample. Methods for high-throughput genetic screening are also provided. In yet another aspect, the present invention provides single-stranded oligonucleotide DNA primers for amplification of a target DNA sequence in a multiplex polymerase chain reaction.

34 Claims, 6 Drawing Sheets

Cystic Fibrosis Transmembrane Regulator(CFTR) 15-plex

Primer Sequences

| Sequence | Exon | Size (bp) |
|---|---|---|
| AGG CTT CTC AGT GAT CTG TTG<br>GAA TCA TTC AGT GGG TAT AAG CAG | Int 19 | ~440 |
| GCC CGA CAA ATA ACC AAG TGA<br>AGT CTA ACA AAG CAA GCA GTG | 19 | 410 |
| TGA TGG TAA GTA CAT GGG TG<br>CAA AAG TAC CTG TTG CTC CA | 21 | 381 |
| CTT CTA ATG GTG ATG ACA GCC T<br>CCA CTG AAA ATA TGA GGA AAT | 9 | 335 |
| AGG TAG CAG CTA TTT TTA TGG<br>TAA GGG AGT CTT TTG CAC AA | 13 | 295 |
| TGT AGG AAG TCA CCA AAG<br>CGA TAC AGA ATA TAT GTG CC | 4 | 267 |
| GGA GTC CAA TTT TCA CTC ATC TTG T<br>AGT TAA TGA GTT CAT AGT ACC TGT T | 17b | 245 |
| AGA TAC TTC AAT AGC TCA GCC<br>GGT ACA TTA CCT GTA TTT TGT TT | 7 | 220 |
| CAG ATT GAG CAT ACT AAA AGT G<br>TAC ATG AAT GAC ATT TAC AGC A | 11 | 200 |
| GAG CCT TCA GAG GGT AAA AT | 10 | 175 |

Gauchers(GCR) and Sickle Cell Anemia(SCA) 4-plex

GCR Primer Sequences

| Sequence | Exon | Size (bp) |
|---|---|---|
| GGG TGG GAG GGT GGA GGC TAA TGG<br>CCA GAA GGT AGA AAG GTG AG | 6 | 401 |
| GAA TGT CCC AAG CCT TTG A<br>AAG CTG AAG CAA GAG AAT CG | 2 | 358 |
| TGC AAC TAC TGA GGC ACT T<br>TAC AAT GAT GGG ACT GTC G | 9 | 319 |

SCA Primer Sequences

| Sequence | Exon | Size (bp) |
|---|---|---|
| CAT TTG CTT CTG ACA CAA CTG<br>CCA ACT TCA TCC ACG TTC ACC | | 124 |

GCR and Tay-Sachs (TS) 3-plex

GCR

| Sequence | Exon | Size (bp) |
|---|---|---|
| CCT TGC CCT GAA CCC CGA A<br>CTG ACT CTG TCC CTT TAA TGC CCA | 9, 10, 11 | 871 |

TS Primer Sequences

| Sequence | Exon | Size (bp) |
|---|---|---|
| GTG TGG CGA GAG GAT ATT CCA<br>TGG CTA GAT GGG ATT GGG TCT | 11, 12*** | 530 |
| GGG TCC TAC AAC CCT GTC ACC CAC<br>AAG CTT CAC TCT GAG CAT AAC AAG | 7*** | 190 |

B-thalassemia Primer Sequences

| Sequence | Exon | Size (bp) |
|---|---|---|
| GCT GTC ATC ACT TAG ACC TC<br>GCA AGA AAG CGA GCT TAG TG | 1, 2, 3 | 1612 |

| Exon | Size (bp) |
|---|---|
| 20 | 155 |
| 5 | 132 |
| 14b | 110 |
| 12 | 90 |
| 3 | 70 |

```
AAG AAC TGG ATC AGG GAA GA
TCC TTT TGC TCA CCT GTG GT

GCT GTC AAG CCG TGT TCT A
GTA TAA TTT ATA ACA ATA GTG CC

TTG GTG GTG CTG TGG CTC CT
ACA ATA CAT ACA AAC ATA GTG G

GAC TCT CCT TTT GGA TAC CTA
GCA TGA GCA TTA TAA GTA AGG

GGC GAT GTT TTT TCT GGA GA
ACA AAT GAG ATC CTT ACC CC
```

| Name | Size (bp) |
|---|---|
| SS#1 | 477 |
| SS#2 | 389 |
| SS#3 | 381 |

CFTR Exon 21 Primer Sequences
```
CAA GTG AAT CCT GAG CGT GAT TT
CAA AAG TAC CTG TTG CTC CA

GAA CTT GAT GGT AAG TAC ATG GGT G
AGT CAA AAG TAC TTG CTC CAG

TGA TGG TAA CAT GGG TG
GAA AAG TAC CTG TTG CTC CA
```

| | Name | Size (bp) |
|---|---|---|
| | B* | 204 |
| | F | 186 |
| | H* | 262 |
| | J | 167 |
| | N* | 176 |
| | O* | 211 |

WT-1 Primer Sequences
```
CTG AGT GAA TGG AGC GGC
GGG TGA ATG AGT AGG TGG

CGG TGC TGG ACT TTG CG
AAG TGG ACA GTG AAG GCG

CCG TCT TGC GAG AGC ACC
CTA ATT TGC TGT GGG TTA GG

AGT TGT GTA TAT TTG TGG TTA TG
GTT ACT GTG GAA AGG CAA TG

GAG ATC CCC TTT TCC AG
CAC AGC TGC CAG CAA TG

CTC ACT GTG CCC ACA TTG
CAA TTT CAT TCC ACA ATA G
```

*: Reported previously by Varanasi et al 1994.
**: Reported previously by Navon & Proia 1989.
***: Reported previously by Tanaka et al 1990.

NOTE:
Amplicon sizes increase by 40bp for chimeric primers.

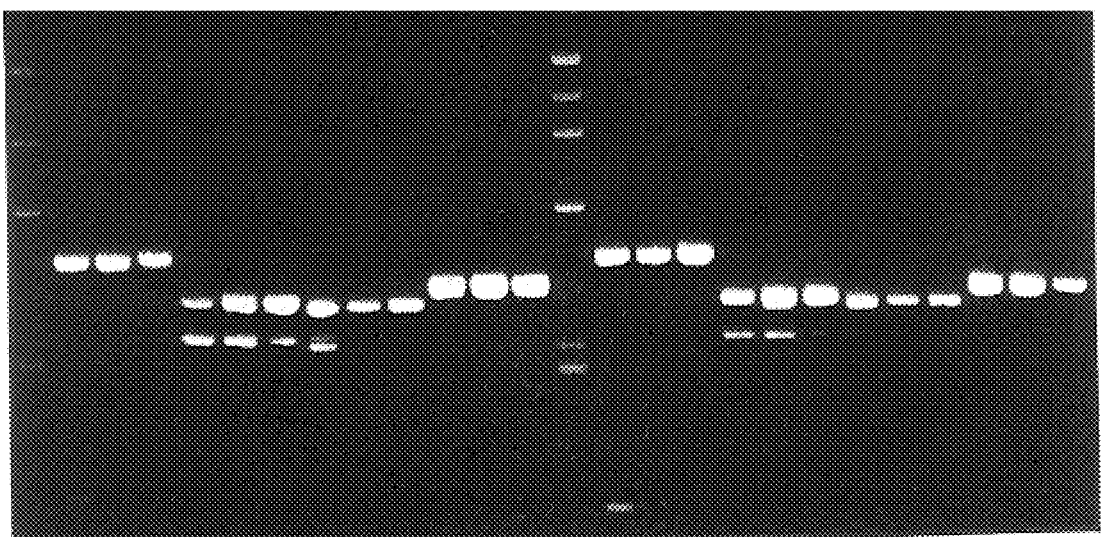
FIG. 2A  FIG. 2B
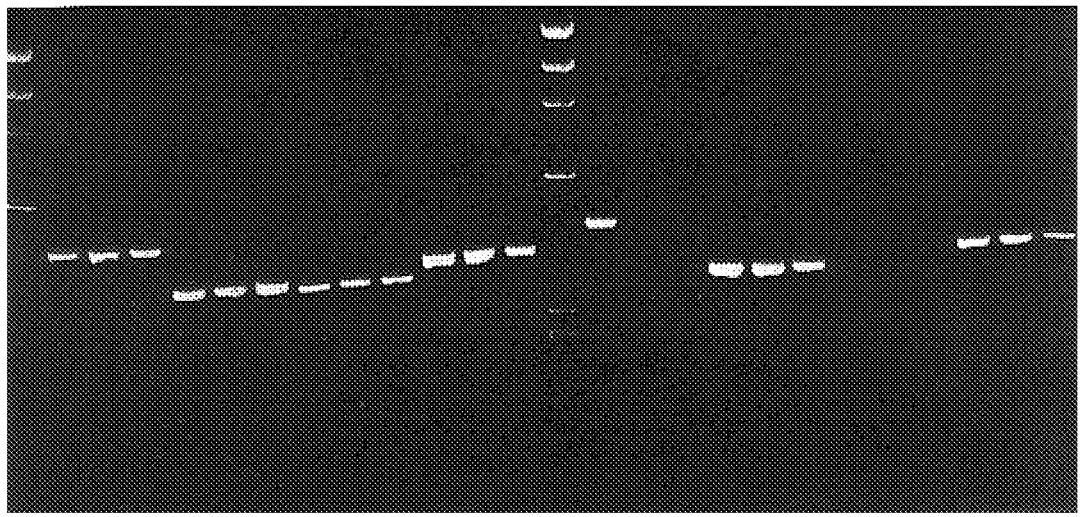
FIG. 2C  FIG. 2D

SEQUENCE LISTING (1) GENERAL INFORMATION:

(iii) NUMBER OF SEQUENCES: 95

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Oligonucleotide primer"

(xi) SEQUENCE DESCRIPTION: SEQ ID NO:1:

GCGGTCCCAA AAGGGTCAGT                                            20

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Oligonucleotide primer"

(xi) SEQUENCE DESCRIPTION: SEQ ID NO:2:

CGCCAGGGTT TTCCCAGTCA                                            20

(2) INFORMATION FOR SEQ ID NO:3:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Oligonucleotide primer"

(xi) SEQUENCE DESCRIPTION: SEQ ID NO:3:

CGCCAGGGGG GGCCCAGTCA                                               20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(xi) SEQUENCE DESCRIPTION: SEQ ID NO:4:

CGGCAGCGGG GCCCAGTCCA                                               20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(xi) SEQUENCE DESCRIPTION: SEQ ID NO:5:

CGCGGCCGGG GCCCATCCCA                                               20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(xi) SEQUENCE DESCRIPTION: SEQ ID NO:6:

CGCGGCCGGG GCCATCTCAA                                               20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(xi) SEQUENCE DESCRIPTION: SEQ ID NO:7:

GAGGCCGGTG GCCATGTCAA                                               20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(xi) SEQUENCE DESCRIPTION: SEQ ID NO:8:

TAGGCGCGTG GCCATGTCAA                    20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(xi) SEQUENCE DESCRIPTION: SEQ ID NO:9:

TAGGCCCGTG GCCATGTTAA                    20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(xi) SEQUENCE DESCRIPTION: SEQ ID NO:10:

TAGGCCCGTG GCAATATTAA                    20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(xi) SEQUENCE DESCRIPTION: SEQ ID NO:11:

CCGGTCCGTG GCAATATTAA                    20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(xi) SEQUENCE DESCRIPTION: SEQ ID NO:12:

CCGGCTCGTG GCGATGTTAA                    20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(xi) SEQUENCE DESCRIPTION: SEQ ID NO:13:

CCGGCGTGTG CCGATATTAA                                             20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(xi) SEQUENCE DESCRIPTION: SEQ ID NO:14:

CCATGCGTGT GCCGATATTA                                             20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(xi) SEQUENCE DESCRIPTION: SEQ ID NO:15:

CAATGCGGGC GCCGATATTA                                             20

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(xi) SEQUENCE DESCRIPTION: SEQ ID NO:16:

CGATGCGGGA GCCAATATAA                                             20

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(xi) SEQUENCE DESCRIPTION: SEQ ID NO:17:

AGATGCGGTA GCCAATATAA                                             20

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(xi) SEQUENCE DESCRIPTION: SEQ ID NO:18:

GGCGTGCTGA GCCAATATGG                    20

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(xi) SEQUENCE DESCRIPTION: SEQ ID NO:19:

GGCGCGCTGA GCCAATATGG                    20

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(xi) SEQUENCE DESCRIPTION: SEQ ID NO:20:

GGCGCGCCGA GCCAATATGG                    20

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(xi) SEQUENCE DESCRIPTION: SEQ ID NO:21:

GGCGCGCCGA GCTAATATAT                    20

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(xi) SEQUENCE DESCRIPTION: SEQ ID NO:22:

AGCTCGGCGA GCTAATATAT                    20

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (A) DESCRIPTION: /desc = "Oligonucleotide primer"

(xi) SEQUENCE DESCRIPTION: SEQ ID NO:23:

AGCGCGGCCA GCTAAGAGAT                                                    20

(2) INFORMATION FOR SEQ ID NO:24:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Oligonucleotide primer"

(xi) SEQUENCE DESCRIPTION: SEQ ID NO:24:

CGCGCGGCCG GCTGGAGAGA                                                    20

(2) INFORMATION FOR SEQ ID NO:25:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Oligonucleotide primer"

(xi) SEQUENCE DESCRIPTION: SEQ ID NO:25:

CGCGAGGCCG GCTGTAGAGG                                                    20

(2) INFORMATION FOR SEQ ID NO:26:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Oligonucleotide primer"

(xi) SEQUENCE DESCRIPTION: SEQ ID NO:26:

CGCGAGGCCA GCGGCCGAGG                                                    20

(2) INFORMATION FOR SEQ ID NO:27:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Oligonucleotide primer"

(xi) SEQUENCE DESCRIPTION: SEQ ID NO:27:

CGCGAGGCCA GCGGTCGAGG                                                    20

(2) INFORMATION FOR SEQ ID NO:28:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: other nucleic acid
            (A) DESCRIPTION: /desc = "Oligonucleotide primer"

(xi) SEQUENCE DESCRIPTION: SEQ ID NO:28:

CGCGAGGCCA GCGGTCGAGG                                                    20

(2) INFORMATION FOR SEQ ID NO:29:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide primer"

(xi) SEQUENCE DESCRIPTION: SEQ ID NO:29:

CGCGGGGCCC GCGGCCGCGG                                                    20

(2) INFORMATION FOR SEQ ID NO:30:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide primer"

(xi) SEQUENCE DESCRIPTION: SEQ ID NO:30:

CGCCCGCCGC GCCCCGCGCC                                                    20

(2) INFORMATION FOR SEQ ID NO:31:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide primer"

(xi) SEQUENCE DESCRIPTION: SEQ ID NO:31:

GGCGCTCCAT TAGCGTGAGT                                                    20

(2) INFORMATION FOR SEQ ID NO:32:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "CFTR 15-PLEX PRIMER
                 SEQUENCE - int19"

(xi) SEQUENCE DESCRIPTION: SEQ ID NO:32:

AGGCTTCTCA GTGATCTGTT G                                                  21

(2) INFORMATION FOR SEQ ID NO:33:

(i) SEQUENCE CHARACTERISTICS:
            (A) LENGTH: 24 base pairs
            (B) TYPE: nucleic acid
            (C) STRANDEDNESS: single (D) TOPOLOGY: linear (ii) MOLECULE TYPE: other nucleic acid
        (A) DESCRIPTION: /desc = "CFTR 15-PLEX PRIMER
            SEQUENCE - int19"

(xi) SEQUENCE DESCRIPTION: SEQ ID NO:33:

GAATCATTCA GTGGGTATAA GCAG                                              24

(2) INFORMATION FOR SEQ ID NO:34:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR 15-PLEX PRIMER
            SEQUENCE - exon 19"

(xi) SEQUENCE DESCRIPTION: SEQ ID NO:34:

GCCCGACAAA TAACCAAGTG A                                                 21

(2) INFORMATION FOR SEQ ID NO:35:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR 15-PLEX PRIMER
            SEQUENCE - exon 19"

(xi) SEQUENCE DESCRIPTION: SEQ ID NO:35:

AGTCTAACAA AGCAAGCAGT G                                                 21

(2) INFORMATION FOR SEQ ID NO:36:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR 15-PLEX PRIMER
            SEQUENCE - exon 21"

(xi) SEQUENCE DESCRIPTION: SEQ ID NO:36:

TGATGGTAAG TACATGGGTG                                                   20

(2) INFORMATION FOR SEQ ID NO:37:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR 15-PLEX PRIMER
            SEQUENCE - exon 21"

(xi) SEQUENCE DESCRIPTION: SEQ ID NO:37:

CAAAAGTACC TGTTGCTCCA                                                   20

```
(2) INFORMATION FOR SEQ ID NO:38:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR 15-PLEX PRIMER
            SEQUENCE - exon 9"

(xi) SEQUENCE DESCRIPTION: SEQ ID NO:38:

CTTCTAATGG TGATGACAGC CT                                              22

(2) INFORMATION FOR SEQ ID NO:39:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR 15-PLEX PRIMER
            SEQUENCE - exon 9"

(xi) SEQUENCE DESCRIPTION: SEQ ID NO:39:

CCACTGAAAA TAATATGAGG AAAT                                            24

(2) INFORMATION FOR SEQ ID NO:40:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR 15-PLEX PRIMER
            SEQUENCE - exon 13"

(xi) SEQUENCE DESCRIPTION: SEQ ID NO:40:

AGGTAGCAGC TATTTTTATG G                                               21

(2) INFORMATION FOR SEQ ID NO:41:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR 15-PLEX PRIMER
            SEQUENCE - exon 13"

(xi) SEQUENCE DESCRIPTION: SEQ ID NO:41:

TAAGGGAGTC TTTTGCACAA                                                 20

(2) INFORMATION FOR SEQ ID NO:42:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR 15-PLEX PRIMER
            SEQUENCE - exon 4"
```

(xi) SEQUENCE DESCRIPTION: SEQ ID NO:42:

TGTAGGAAGT CACCAAAG                                                   18

(2) INFORMATION FOR SEQ ID NO:43:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR 15-PLEX PRIMER
            SEQUENCE - exon 4"

(xi) SEQUENCE DESCRIPTION: SEQ ID NO:43:

CGATACAGAA TATATGTGCC                                                 20

(2) INFORMATION FOR SEQ ID NO:44:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR 15-PLEX PRIMER
            SEQUENCE - exon 17b"

(xi) SEQUENCE DESCRIPTION: SEQ ID NO:44:

GGAGTCCAAT TTTCACTCAT CTTG                                            24

(2) INFORMATION FOR SEQ ID NO:45:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR 15-PLEX PRIMER
            SEQUENCE - exon 17b"

(xi) SEQUENCE DESCRIPTION: SEQ ID NO:45:

AGTTAATGAG TTCATAGTAC CTGTT                                           25

(2) INFORMATION FOR SEQ ID NO:46:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR 15-PLEX PRIMER
            SEQUENCE - exxon 7"

(xi) SEQUENCE DESCRIPTION: SEQ ID NO:46:

AGATACTTCA ATAGCTCAGC C                                               21

(2) INFORMATION FOR SEQ ID NO:47:

(i) SEQUENCE CHARACTERISTICS:
        (A) LENGTH: 23 base pairs
        (B) TYPE: nucleic acid (C) STRANDEDNESS: single
        (D) TOPOLOGY: linear (ii) MOLECULE TYPE: other nucleic acid
        (A) DESCRIPTION: /desc = "CFTR 15-PLEX PRIMER
            SEQUENCE - exon 7"

(xi) SEQUENCE DESCRIPTION: SEQ ID NO:47:

GGTACATTAC CTGTATTTTG TTT                                              23

(2) INFORMATION FOR SEQ ID NO:48:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR 15-PLEX PRIMER
            SEQUENCE - exon 11"

(xi) SEQUENCE DESCRIPTION: SEQ ID NO:48:

CAGATTGAGC ATACTAAAAG TG                                               22

(2) INFORMATION FOR SEQ ID NO:49:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR 15-PLEX PRIMER
            SEQUENCE - exon 11"

(xi) SEQUENCE DESCRIPTION: SEQ ID NO:49:

TACATGAATG ACATTTACAG CA                                               22

(2) INFORMATION FOR SEQ ID NO:50:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR 15-PLEX PRIMER
            SEQUENCE - exon 10"

(xi) SEQUENCE DESCRIPTION: SEQ ID NO:50:

GAGCCTTCAG AGGGTAAAAT                                                  20

(2) INFORMATION FOR SEQ ID NO:51:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR 15-PLEX PRIMER
            SEQUENCE - exon 10"

(xi) SEQUENCE DESCRIPTION: SEQ ID NO:51:

TCACATAGTT TCTTACCTCT                                                  20

(2) INFORMATION FOR SEQ ID NO:52:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR 15-PLEX PRIMER
            SEQUENCE - exon 20"

(xi) SEQUENCE DESCRIPTION: SEQ ID NO:52:

AAGAACTGGA TCAGGGAAGA                                               20

(2) INFORMATION FOR SEQ ID NO:53:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR 15-PLEX PRIMER
            SEQUENCE - exon 20"

(xi) SEQUENCE DESCRIPTION: SEQ ID NO:53:

TCCTTTTGCT CACCTGTGGT                                               20

(2) INFORMATION FOR SEQ ID NO:54:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR 15-PLEX PRIMER
            SEQUENCE - exon 5"

(xi) SEQUENCE DESCRIPTION: SEQ ID NO:54:

GCTGTCAAGC CGTGTTCTA                                                19

(2) INFORMATION FOR SEQ ID NO:55:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR 15-PLEX PRIMER
            SEQUENCE - exon 5"

(xi) SEQUENCE DESCRIPTION: SEQ ID NO:55:

GTATAATTTA TAACAATAGT GCC                                           23

(2) INFORMATION FOR SEQ ID NO:56:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR 15-PLEX PRIMER

```
            SEQUENCE - exon 14b"

(xi) SEQUENCE DESCRIPTION: SEQ ID NO:56:

TTGGTTGTGC TGTGGCTCCT                                              20

(2) INFORMATION FOR SEQ ID NO:57:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR 15-PLEX PRIMER
            SEQUENCE - exon 14b"

(xi) SEQUENCE DESCRIPTION: SEQ ID NO:57:

ACAATACATA CAAACATAGT GG                                           22

(2) INFORMATION FOR SEQ ID NO:58:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR 15-PLEX PRIMER
            SEQUENCE - exon 12"

(xi) SEQUENCE DESCRIPTION: SEQ ID NO:58:

GACTCTCCTT TTGGATACCT A                                            21

(2) INFORMATION FOR SEQ ID NO:59:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR 15-PLEX PRIMER
            SEQUENCE - exon 12"

(xi) SEQUENCE DESCRIPTION: SEQ ID NO:59:

GCATGAGCAT TATAAGTAAG G                                            21

(2) INFORMATION FOR SEQ ID NO:60:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR 15-PLEX PRIMER
            SEQUENCE - exon 3"

(xi) SEQUENCE DESCRIPTION: SEQ ID NO:60:

GGCGATGTTT TTTCTGGAGA                                              20

(2) INFORMATION FOR SEQ ID NO:61:

(i) SEQUENCE CHARACTERISTICS:
        (A) LENGTH: 20 base pairs
```

(B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR 15-PLEX PRIMER
            SEQUENCE - exon 3"

(xi) SEQUENCE DESCRIPTION: SEQ ID NO:61:

ACAAATGAGA TCCTTACCCC                                                    20

(2) INFORMATION FOR SEQ ID NO:62:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR EXON 21 PRIMER
            SEQUENCE - SS#1"

(xi) SEQUENCE DESCRIPTION: SEQ ID NO:62:

CAAGTGAATC CTGAGCGTGA TTT                                                23

(2) INFORMATION FOR SEQ ID NO:63:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR EXON 21 PRIMER
            SEQUENCE - SS#1"

(xi) SEQUENCE DESCRIPTION: SEQ ID NO:63:

CAAAAGTACC TGTTGCTCCA                                                    20

(2) INFORMATION FOR SEQ ID NO:64:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR EXON 21 PRIMER
            SEQUENCE - SS#2"

(xi) SEQUENCE DESCRIPTION: SEQ ID NO:64:

GAACTTGATG GTAAGTACAT GGGTG                                              25

(2) INFORMATION FOR SEQ ID NO:65:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR EXON 21 PRIMER
            SEQUENCE - SS#2"

(xi) SEQUENCE DESCRIPTION: SEQ ID NO:65:

AGTCAAAAGT ACCTGTTGCT CCAG                                               24

(2) INFORMATION FOR SEQ ID NO:66:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR EXON 21 PRIMER
            SEQUENCE -SS#3"

(xi) SEQUENCE DESCRIPTION: SEQ ID NO:66:

TGATGGTAAG TACATGGGTG                                          20

(2) INFORMATION FOR SEQ ID NO:67:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "CFTR EXON 21 PRIMER
            SEQUENCE - SS#3"

(xi) SEQUENCE DESCRIPTION: SEQ ID NO:67:

CAAAAGTACC TGTTGCTCCA                                          20

(2) INFORMATION FOR SEQ ID NO:68:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "GCR 4-PLEX PRIMER SEQUENCE
            - exon 6"

(xi) SEQUENCE DESCRIPTION: SEQ ID NO:68:

GGGTGGGAGG GTGGAGGCTA ATGG                                     24

(2) INFORMATION FOR SEQ ID NO:69:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "GCR 4-PLEX PRIMER SEQUENCE
            - exon 6"

(xi) SEQUENCE DESCRIPTION: SEQ ID NO:69:

CCAGAAGGTA GAAAGGTGAG                                          20

(2) INFORMATION FOR SEQ ID NO:70:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid

```
        (A) DESCRIPTION: /desc = "GCR 4-PLEX PRIMER SEQUENCE
            - exon 2"

(xi) SEQUENCE DESCRIPTION: SEQ ID NO:70:

GAATGTCCCA AGCCTTTGA                                                  19

(2) INFORMATION FOR SEQ ID NO:71:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "GCR 4-PLEX PRIMER SEQUENCE
            - exon 2"

(xi) SEQUENCE DESCRIPTION: SEQ ID NO:71:

AAGCTGAAGC AAGAGAATCG                                                 20

(2) INFORMATION FOR SEQ ID NO:72:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "GCR 4-PLEX PRIMER SEQUENCE
            - exon 9"

(xi) SEQUENCE DESCRIPTION: SEQ ID NO:72:

TGCAACTACT GAGGCACTT                                                  19

(2) INFORMATION FOR SEQ ID NO:73:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "GCR 4-PLEX PRIMER SEQUENCE
            - exon 9"

(xi) SEQUENCE DESCRIPTION: SEQ ID NO:73:

TACAATGATG GGACTGTCG                                                  19

(2) INFORMATION FOR SEQ ID NO:74:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SCA 4-PLEX PRIMER SEQUENCE
            - exon 9"

(xi) SEQUENCE DESCRIPTION: SEQ ID NO:74:

CATTTGCTTC TGACACAACT G                                               21

(2) INFORMATION FOR SEQ ID NO:75:

(i) SEQUENCE CHARACTERISTICS:
```

(A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SCA 4-PLEX PRIMER SEQUENCE
            - exon 9"

(xi) SEQUENCE DESCRIPTION: SEQ ID NO:75:

CCAACTTCAT CCACGTTCAC C                                              21

(2) INFORMATION FOR SEQ ID NO:76:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "GCR 3-PLEX PRIMER SEQUENCE
            - exons 9, 10, 11"

(xi) SEQUENCE DESCRIPTION: SEQ ID NO:76:

CCTTGCCCTG AACCCCGAA                                                 19

(2) INFORMATION FOR SEQ ID NO:77:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "GCR 3-PLEX PRIMER SEQUENCE
            - exons 9, 10, 11"

(xi) SEQUENCE DESCRIPTION: SEQ ID NO:77:

CTGACTCTGT CCCTTTAATG CCCA                                           24

(2) INFORMATION FOR SEQ ID NO:78:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "TS 3-PLEX PRIMER SEQUENCE -
            exons 11, 12"

(xi) SEQUENCE DESCRIPTION: SEQ ID NO:78:

GTGTGGCGAG AGGATATTCC A                                              21

(2) INFORMATION FOR SEQ ID NO:79:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "TS 3-PLEX PRIMER SEQUENCE -
            exons 11, 12"

(xi) SEQUENCE DESCRIPTION: SEQ ID NO:79:

```
TGGCTAGATG GGATTGGGTC T                                              21

(2) INFORMATION FOR SEQ ID NO:80:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "TS 3-PLEX PRIMER SEQUENCE -
            exon 7"

(xi) SEQUENCE DESCRIPTION: SEQ ID NO:80:

GGGTCCTACA ACCCTGTCAC CCAC                                           24

(2) INFORMATION FOR SEQ ID NO:81:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "TS 3-PLEX PRIMER SEQUENCE -
            exon 7"

(xi) SEQUENCE DESCRIPTION: SEQ ID NO:81:

AAGCTTCACT CTGAGCATAA CAAG                                           24

(2) INFORMATION FOR SEQ ID NO:82:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "B-THALASSEMIA PRIMER
            SEQUENCE - exons 1, 2, 3"

(xi) SEQUENCE DESCRIPTION: SEQ ID NO:82:

GCTGTCATCA CTTAGACCTC                                                20

(2) INFORMATION FOR SEQ ID NO:83:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "B-THALASSEMIA PRIMER
            SEQUENCE - exons 1, 2, 3"

(xi) SEQUENCE DESCRIPTION: SEQ ID NO:83:

GCAAGAAAGC GAGCTTAGTG                                                20

(2) INFORMATION FOR SEQ ID NO:84:

(i) SEQUENCE CHARACTERISTICS:
        (A) LENGTH: 18 base pairs
        (B) TYPE: nucleic acid
        (C) STRANDEDNESS: single
        (D) TOPOLOGY: linear
```

```
    (ii) MOLECULE TYPE: other nucleic acid
         (A) DESCRIPTION: /desc = "WT-1 PRIMER SEQUENCE - B"

(xi) SEQUENCE DESCRIPTION: SEQ ID NO:84:

CTGAGTGAAT GGAGCGGC                                                    18

(2) INFORMATION FOR SEQ ID NO:85:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "WT-1 PRIMER SEQUENCE - B"

(xi) SEQUENCE DESCRIPTION: SEQ ID NO:85:

GGGTGAATGA GTAGGTGG                                                    18

(2) INFORMATION FOR SEQ ID NO:86:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "WT-1 PRIMER SEQUENCE - F"

(xi) SEQUENCE DESCRIPTION: SEQ ID NO:86:

CGGTGCTGGA CTTTGCG                                                     17

(2) INFORMATION FOR SEQ ID NO:87:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "WT-1 PRIMER SEQUENCE - F"

(xi) SEQUENCE DESCRIPTION: SEQ ID NO:87:

AAGTGGACAG TGAAGGCG                                                    18

(2) INFORMATION FOR SEQ ID NO:88:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "WT-1 PRIMER SEQUENCE - H"

(xi) SEQUENCE DESCRIPTION: SEQ ID NO:88:

CCGTCTTGCG AGAGCACC                                                    18

(2) INFORMATION FOR SEQ ID NO:89:

(i) SEQUENCE CHARACTERISTICS:
         (A) LENGTH: 20 base pairs
         (B) TYPE: nucleic acid
         (C) STRANDEDNESS: single
         (D) TOPOLOGY: linear
```

(ii) MOLECULE TYPE: other nucleic acid
            (A) DESCRIPTION: /desc = "WT-1 PRIMER SEQUENCE - H"

(xi) SEQUENCE DESCRIPTION: SEQ ID NO:89:

CTAATTTGCT GTGGGTTAGG                                           20

(2) INFORMATION FOR SEQ ID NO:90:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "WT-1 PRIMER SEQUENCE - J"

(xi) SEQUENCE DESCRIPTION: SEQ ID NO:90:

AGTTGTGTAT ATTTGTGGTT ATG                                       23

(2) INFORMATION FOR SEQ ID NO:91:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "WT-1 PRIMER SEQUENCE - J"

(xi) SEQUENCE DESCRIPTION: SEQ ID NO:91:

GTTACTGTGG AAAGGCAATG                                           20

(2) INFORMATION FOR SEQ ID NO:92:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "WT-1 PRIMER SEQUENCE - N"

(xi) SEQUENCE DESCRIPTION: SEQ ID NO:92:

GAGATCCCCT TTTCCAG                                              17

(2) INFORMATION FOR SEQ ID NO:93:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "WT-1 PRIMER SEQUENCE - N"

(xi) SEQUENCE DESCRIPTION: SEQ ID NO:93:

CACAGCTGCC AGCAATG                                              17

(2) INFORMATION FOR SEQ ID NO:94:

(i) SEQUENCE CHARACTERISTICS:
        (A) LENGTH: 18 base pairs
        (B) TYPE: nucleic acid
        (C) STRANDEDNESS: single -continued

```
        (D) TOPOLOGY: linear (ii) MOLECULE TYPE: other nucleic acid
        (A) DESCRIPTION: /desc = "WT-1 PRIMER SEQUENCE - 0"

(xi) SEQUENCE DESCRIPTION: SEQ ID NO:94:

CTCACTGTGC CCACATTG                                                    18

(2) INFORMATION FOR SEQ ID NO:95:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "WT-1 PRIMER SEQUENCE - 0"

(xi) SEQUENCE DESCRIPTION: SEQ ID NO:95:

CAATTTCATT CCACAATAG                                                   19
```

UNIVERSAL PRIMER SEQUENCE FOR MULTIPLEX DNA AMPLIFICATION

This application is a 371 of PCT/US96/09637, filed Jun. 6, 1996, and a continuation-in-part of Ser. No. 08/474,450, filed Jun. 7, 1995, now U.S. Pat. No. 5,882,856.

FIELD OF THE INVENTION

This invention pertains to universal primers having use in amplification of DNA sequences by methods such as polymerase chain reaction (PCR), specifically to primers that allow the simultaneous amplification of a multiplicity of DNA sequences.

BACKGROUND OF THE INVENTION

Polymerase chain reaction (PCR) is a method whereby virtually any DNA sequence can be selectively amplified. The method involves using paired sets of oligonucleotides of predetermined sequence that hybridize to opposite strands of DNA and define the limits of the sequence to be amplified. The oligonucleotides prime multiple sequential rounds of DNA synthesis catalyzed by a thermostable DNA polymerase. Each round of synthesis is typically separated by a melting and re-annealing step, allowing a given DNA sequence to be amplified several hundred-fold in less than an hour (Saiki et al., *Science* 239:487, 1988).

With the rapid advances in mammalian molecular genetics, an ever increasing number of disease genes have been identified. Accordingly, PCR has gained widespread use for the diagnosis of inherited disorders and the susceptibility to disease. Typically, the region of interest is amplified from either genomic DNA or from a source of specific cDNA encoding the cognate gene product. Mutations or polymorphisms are then identified by subjecting the amplified DNA to analytical techniques such as DNA sequencing, hybridization with allele-specific oligonucleotides (ASOs), oligonucleotide ligation, restriction endonuclease cleavage or single-strand conformational polymorphism (SSCP) analysis.

For the analysis of small genes and transcripts, or genes where the mutant allele or polymorphism is well characterized, amplification of a single defined region of DNA is sometimes sufficient. When analyzing large genes and transcripts or undefined genes, however, multiple individual PCR reactions are often required to identify critical base changes or deletions. Thus, to streamline the analysis of large complex genes, multiplex PCR (i.e., the simultaneous amplification of different target DNA sequences in a single PCR reaction) has been utilized.

The results obtained with multiplex PCR are, however, frequently complicated by artifacts of the amplification procedure. These include "false-negative" results due to reaction failure and "false-positive" results such as the amplification of spurious products, which may be caused by annealing of the primers to sequences which are related to, but distinct from, the true recognition sequences.

For use in multiplex PCR, a primer should be designed so that its predicted hybridization kinetics are similar to those of the other primers used in the same multiplex reaction. While the annealing temperatures and primer concentrations may be calculated to some degree, conditions generally have to be empirically determined for each multiplex reaction. Since the possibility of non-specific priming increases with each additional primer pair, conditions must be modified as necessary as individual primer sets are added. Moreover, artifacts that result from competition for resources (e.g., depletion of primers) are augmented in multiplex PCR, since differences in the yields of unequally amplified fragments are enhanced with each cycle.

Weighardt et al. (*PCR Meth.App.* 3:77, 1993) describe the use of 5'-tailed oligonucleotides for PCR. However, a key feature of this amplification method involves separate annealing and primer extension reactions for each primer, which is not practical in a multiplex context. Therefore, complete optimization of the reaction conditions for multiplex PCR can become labor intensive and time consuming. Since different multiplex PCRs may each have unique reaction conditions, development of new diagnostic tests can become very costly.

Thus, there is a need in the art for primers that allow multiplex PCR reactions to be designed and carried out without elaborate optimization steps, irrespective of the potentially divergent properties of the different primers used. Furthermore, there is a need in the art for primers that allow multiplex PCR reactions that, under the same reaction conditions, simultaneously produce equivalent amounts of each of many amplification products.

SUMMARY OF THE INVENTION

This invention pertains to primers that allow simultaneous amplification of multiple DNA target sequences present in a DNA sample. According to the invention, the DNA sample in a single reaction mixture is contacted with a multiplicity of paired oligonucleotide primers having the structure 5'-XY-3', wherein: X comprises a sequence that does not hybridize to the target sequence; the melting temperature of a hybrid between X and its complement in the absence of other sequences is greater than about 60° C.; and Y comprises a sequence contained within or flanking the target sequence or its complement.

Multiple cycles of melting, reannealing, and DNA synthesis (i.e., a PCR reaction) are thereafter performed with the above mentioned DNA sample and invention oligonucleotide primers. Amplified target sequences may then be detected by any method, including, for example, hybridization with allele-specific oligonucleotides, restriction endonuclease cleavage, or single-strand conformational polymorphism (SSCP) analysis.

The invention also encompasses a method for detecting multiple defined target DNA sequences in a DNA sample. This method is carried out by performing the same procedure set forth above, in which the 3' sequence of one primer of each pair comprises a target DNA sequence itself or its complement. The method includes a further step of detecting the amplification products, preferably by gel electrophoresis. In this embodiment, the presence or absence of an amplification product is diagnostic of the presence or absence of the target sequence in the original DNA sample.

In another aspect, the invention encompasses methods for high-throughput genetic screening. The method, which allows the rapid and simultaneous detection of multiple defined target DNA sequences in DNA samples obtained from a multiplicity of individuals, is carried out by simultaneously amplifying many different target sequences from a large number of patient DNA samples, using oligonucleotide primer pairs as above.

In yet another aspect, the present invention provides single-stranded oligonucleotide DNA primers for amplification of a target DNA sequence in a multiplex polymerase chain reaction. The primers have the structure 35 5'-XY-3', wherein X comprises an invention primer sequence, and Y comprises a sequence contained within or flanking a target sequence or its complement. Typically, Y comprises a sequence from 17 to 25 bases in length, and the melting temperature of hybrids between the primers and their complements is at least 72° C.

The methods and compositions of the present invention can be applied to the diagnosis of genetic and infectious diseases, gender determination, genetic linkage analysis, and forensic studies.

BRIEF DESCRIPTION OF THE DRAWINGS

FIGS. 1A and 1B are a table listing amplicon-specific oligonucleotide primer sequences.

FIGS. 2A through 2D show agarose gel analysis of primer concentration and annealing temperature for amplification of CFTR exon 21.

DETAILED DESCRIPTION OF THE INVENTION

Figure 3:
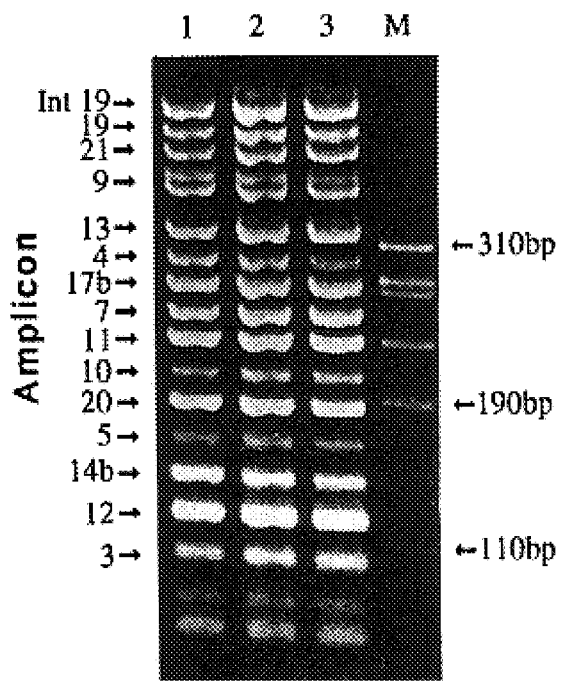
FIG. 3 shows agarose gel analysis of CFTR 15-plex amplicon organization.

Invention methods described herein provide an amplification system for multiplex PCR which is based on the use of chimeric primers tagged on the 5' end with an unrelated 20 nucleotide sequence (UPS). The examples provided below demonstrate that multiple genomic sequences can be co-amplified under identical reaction conditions and cycling parameters with very little optimization of PCR conditions. Using invention compositions and methods, highly specific and efficient amplification of target sequences can be easily and reproducibly achieved by simple adjustment of the individual primer concentrations, with no additional modification of either the reaction components or annealing temperatures.

Invention chimeric primers produced clean visibly detectable PCR profiles over an 8-fold range of template DNA concentrations (see examples). Moreover, the high level of consistency, with respect to the relative band intensities, increases the informativeness and simplifies the interpretation of the results.

The enhanced specificity and efficiency which is conferred by using invention chimeric primers is due to a normalization of the hybridization kinetics. During the early rounds of the PCR, molecules are synthesized which contain the tagged primers at their 5' ends. Therefore, in all subsequent rounds of amplification, the amplicons synthesized will all have identical 20 bp priming sequences with the predicted hybridization kinetics of the universal primer sequence (UPS) tag. Further, by virtue of the extremely GC-rich region at the 5' end of invention UPS sequences, under PCR conditions optimal for the UPS tag, nucleation is progressing in a primer oriented 5' to 3' direction. In addition, each chimeric primer pair has a 3' sequence-specific region with an internal stability profile (ΔG) for primer duplexing lower than the UPS tag. Therefore, chimeric primers, which have an overall Tm significantly greater than 72° C. serve as highly efficient yet stringent recognition sequences for the subsequent rounds of the PCR.

Through normalizing hybridization kinetics, invention compositions and methods have largely eliminated the need to evaluate diverse reaction conditions and cycling parameters. Therefore, the use of invention UPS-tagged primers provides a less costly method in terms of polymerase, labor and time, and should greatly simplify the development of complex multiplex PCRs to be used in new diagnostic tests.

Definitions

1. "Amplification" of DNA as used herein denotes the use of polymerase chain reaction (PCR) to increase the concentration of a particular DNA sequence within a mixture of DNA sequences. An "amplicon" is a target DNA sequence that is amplified by PCR.

2. "Multiplex PCR" as used herein refers to the simultaneous amplification of multiple DNA targets in a single polymerase chain reaction (PCR) mixture.

3. "High-throughput" denotes the ability to simultaneously process and screen a large number of DNA samples (e.g. in excess of 100 genomic DNAs) in a rapid and economical manner, as well as to simultaneously screen large numbers of different genetic loci within a single DNA sample.

4. "$T_m$" as used herein, refers to the melting temperature (temperature at which 50% of the oligonucleotide is a duplex) of the oligonucleotide calculated using the nearest-neighbor thermodynamic values of Breslauer et al. (*Proc. Natl. Acad. Sci. USA* 83:3746–3750, 1986) for DNA and Freier et al. (*Proc. Natl. Acad. Sci. USA* 83:9373–9377, 1986) for RNA.

5. "ΔG" as used herein, refers to the free energy for the oligonucleotide as calculated by the nearest neighbor method of Breslauer et al. (DNA) and Freier et al. (RNA). The free energy is calculated by the formula: G=H−TS; where H is the enthalpy, S is the entropy and T is the temperature. The free energy is a measure of stability, the greater the negative value, the more stable the duplex formed by the oligonucleotide.

The present invention encompasses methods and compositions that allow the efficient and essentially simultaneous amplification of different target DNA sequences in a single polymerase chain reaction (i.e., multiplex PCR). Preferably, equivalent amounts of each amplification product are obtained. The method utilizes novel chimeric oligonucleotide primers that circumvent the technical difficulties associated with multiplex PCR that result in unequal amplification of different target sequences in the same reaction mix.

For example, in a standard PCR reaction employing more than a single pair of oligonucleotide primers, the obligatory imposition of a single-set of reaction conditions generally means that one of the primer sets will function more efficiently in priming, causing the target sequence specified by that set of primers to be selectively amplified in the early cycles of amplification. Furthermore, the more efficient primers will also be depleted from the reaction sooner than the less efficient ones, resulting in the increased accumulation of non-specific amplification products in later cycles of amplification. Clearly, these problems are magnified when it is desired to use multiple primer pairs (>3–4) in a single reaction.

The methods and compositions of the present invention circumvent these problems by imposing a uniformly high degree of specificity on the annealing reactions that occur between different primers present in the mixture and their cognate target sequences in the DNA template. During the early cycles of amplification, products are synthesized that contain the chimeric primers on either end. The chimeric primers then serve as high stringency recognition sequences for subsequent rounds of amplification. This results in normalizing the annealing efficiency of different primers and their cognate target sequences, and thus also normalizes the degree of amplification of different targets.

Primer Design

Multiplex PCR according to present invention utilizes chimeric oligonucleotide primers that include two domains. The 5' "half" of each primer may comprise any sequence between 17 and 25 bases in length that is unrelated to the target DNA, and has the property of forming hybrids with relatively high melting temperatures (e.g., $T_m$s>60° C. in the absence of other sequences). In some applications, when the target DNA sequence is embedded in a sequence of low complexity (i.e., <108 bp), primers may be used that form hybrids with lower melting temperatures.

In one embodiment, the 5' sequence comprises 5'-GCGGTCCCAAAAGGGTCAGT-3'(SEQ ID NO:1). This sequence, which is designated as a "universal primer sequence" (UPS), is derived from the bacteriophage vector M13mp18 (Messing J., *Meth. Enzymol.* 101:20, 1983). Alternative embodiments of invention universal primer sequences for the 5' sequence comprise the following oligonucleotides:

1: 5'-CGC CAG GGT TTT CCC AGT CA-3' (SEQ ID NO:2)
2: 5'-CGC CAG GGG GGG CCC AGT CA-3' (SEQ ID NO:3)
3: 5'-CGG CAG CGG GGC CCA GTC CA-3' (SEQ ID NO:4)
4: 5'-CGC GGC CGG GGC CCA TCC CA-3' (SEQ ID NO:5)
5: 5'-CGC GGC CGG GGC CAT CTC AA-3' (SEQ ID NO:6)
6: 5'-GAG GCC GGT GGC CAT GTC AA-3' (SEQ ID NO:7)
7: 5'-TAG GCG CGT GGC CAT GTC AA-3' (SEQ ID NO:8)
8: 5'-TAG GCC CGT GGC CAT GTT AA-3' (SEQ ID NO:9)
9: 5'-TAG GCC CGT GGC AAT ATT AA-3' (SEQ ID NO:10)
10: 5'-CCG GTC CGT GGC AAT ATT AA-3' (SEQ ID NO:11)
11: 5'-CCG GCT CGT GGC GAT GTT AA-3' (SEQ ID NO:12)
12: 5'-CCG GCG TGT GCC GAT ATT AA-3' (SEQ ID NO:13)
13: 5'-CCA TGC GTG TGC CGA TAT TA-3' (SEQ ID NO:14)
14: 5'-CAA TGC GGG CGC CGA TAT TA-3' (SEQ ID NO:15)
15: 5'-CGA TGC GGG AGC CAA TAT AA-3' (SEQ ID NO:16)
16: 5'-AGA TGC GGT AGC CAA TAT AA-3' (SEQ ID NO:17)
17: 5'-GGC GTG CTG AGC CAA TAT GG-3' (SEQ ID NO:18)
18: 5'-GGC GCG CTG AGC CAA TAT GG-3' (SEQ ID NO:19)
19: 5'-GGC GCG CCG AGC CAA TAT GG-3' (SEQ ID NO:20)
20: 5'-GGC GCG CCG AGC TAA TAT AT-3' (SEQ ID NO:21)
21: 5'-AGC TCG GCG AGC TAA TAT AT-3' (SEQ ID NO:22)
22: 5'-AGC GCG GCC AGC TAA GAG AT-3' (SEQ ID NO:23)
23: 5'-CGC GCG GCC GGC TGG AGA GA-3' (SEQ ID NO:24)
24: 5'-CGC GAG GCC GGC TGT AGA GG-3' (SEQ ID NO:25)
25: 5'-CGC GAG GCC AGC GGC CGA GG-3' (SEQ ID NO:26)
26: 5'-CGC GAG GCC AGC GGT CGA GG-3' (SEQ ID NO:27)
27: 5'-CGC GAG GCC AGC GGT CGA GG-3' (SEQ ID NO:28)
28: 5'-CGC GGG GCC CGC GGC CGC GG-3' (SEQ ID NO:29)
29: 5'-CGC CCG CCG CGC CCC GCG CC-3' (SEQ ID NO:30)
30: 5'-GGC GCT CCA TTA GCG TGA GT-3' (SEQ ID NO:31)

The 3' "half" of each primer comprises a target-specific sequence, i.e., a sequence that is either present or potentially present in the target DNA or its complement. These 3' sequences may comprise without limitation any such sequence of 17–25 bases, and preferably 20 bases, irrespective of the melting temperatures of hybrids formed between the isolated sequence and its complement.

In one embodiment, the 3' half of the primer is intended to hybridize with a genomic sequence flanking the target sequence of interest; in this case, the primer is used to amplify the target sequence for subsequent diagnostic tests such as, e.g., hybridization with allele-specific oligonucleotides, restriction endonuclease cleavage, or single-strand conformational polymorphism (SSCP) analysis. For this purpose, the 3' half of the primer must correspond to a sequence known to be present in all DNA samples to be tested (or its complement). Non-limiting examples of 3' primer halves useful in practicing the present invention are shown in FIG. 1.

In another embodiment, the amplification reaction itself serves as the critical diagnostic step. In this case, the 3' sequence of the primer corresponds to a defined wild-type version of a particular amplicon or its complement (or to a variant version or its complement) whose presence or absence is being tested. When such allele-specific sequences are incorporated into chimeric PCR primers according to the present invention, and the chimeric primers are used in amplification reactions, the absence of a given amplification product is considered definitive for the absence of the allele in the DNA sample being tested.

For use in a given multiplex PCR reaction, target-specific primer sequences are typically analyzed as a group to evaluate the potential for fortuitous dimer formation between different primers. This evaluation may be achieved using commercially available computer programs for sequence analysis, such as Gene Runner, Hastings Software Inc. Other variables, such as the preferred concentrations of Mg$^{++}$, dNTPs, polymerase, and primers, are optimized using methods well-known in the art (Edwards et al., *PCR Meth. App.* 3:565,1994).

DNA Templates

Any DNA sample may be used in practicing the present invention, including without limitation eukaryotic, prokaryotic and viral DNA. In a preferred embodiment, the target DNA represents a sample of genomic DNA isolated from a patient. This DNA may be obtained from any cell source or body fluid. Non-limiting examples of cell sources available in clinical practice include blood cells, buccal cells, cervicovaginal cells, epithelial cells from urine, fetal cells, or any cells present in tissue obtained by biopsy. Body fluids include blood, urine, cerebrospinal fluid, semen and tissue exudates at the site of infection or inflammation. DNA is extracted from the cell source or body fluid using any of the numerous methods that are standard in the art. It will be understood that the particular method used to extract DNA will depend on the nature of the source. The preferred amount of DNA to be extracted for use in the present invention is at least 5 pg (corresponding to about 1 cell equivalent of a genome size of 4×10$^9$ base pairs).

Multiplex PCR Reaction Conditions

In practicing the present invention, a DNA sample is contacted with pairs of chimeric oligonucleotide primers under conditions suitable for polymerase chain reaction. Standard PCR reaction conditions may be used, e.g., 1.5 mM MgCl$_2$, 50 mM KCl, 10 mM Tris-HCl, pH 8.3, 200 $\mu$M deoxynucleotide triphosphates (dNTPs), and 25–100 U/ml Taq polymerase (Perkin-Elmer, Norwalk, Conn.).

The concentration of each chimeric primer in the reaction mixture can range from about 0.05 to about 4 $\mu$M. The optimal concentration for primer is evaluated by performing single PCR reactions using each primer pair individually. Similarly, each primer pair is evaluated independently to confirm that all primer pairs to be included in a single multiplex PCR reaction require the same amplification conditions (i.e., temperature, duration of annealing and extension steps). It was found (see example below) that all chimeric primers containing the Ml3 derived UPS as the 5' half of their sequence could be used at a broad range of annealing temperatures (i.e., 50–60° C.).

Multiplex PCR reactions are carried out using manual or automatic thermal cycling. Any commercially available thermal cycler may be used, such as, e.g., Perkin-Elmer 9600 cycler.

Finally, the reaction products are analyzed using any of several methods that are well-known in the art. Preferably, agarose gel electrophoresis is used to rapidly resolve and identify each of the amplified sequences. In a multiplex reaction, different amplified sequences are preferably of distinct sizes and thus can be resolved in a single gel. In one embodiment, the reaction mixture is treated with one or more restriction endonucleases prior to electrophoresis. Alternative methods of product analysis include without limitation dot-blot hybridization with allele-specific oligonucleotides and SSCP.

The following examples are intended to further illustrate the present invention without limiting the invention thereof.

EXAMPLE 1

Primer Design:

Sequence-specific primers were chosen without regard to hairpin formation and having a calculated ΔG for primer duplexing below −10 kcal/mole. The T$_m$ of these primers range from 52° to 68° C. as determined by the A+T/G+C method. To evaluate potential primer dimer formation within a primer set, primers sets were analyzed using Amplify 1.2 software (University of Wisconsin, Department of Genetics, Madison, Wis.). The universal primer sequence (UPS) 5' GCGGTCCCAAAAGGGTCAGT 3' (SEQ ID NO:1) is from bacteriophage M13mpl8.

The UPS-tagged primers contain the 20 nucleotide UPS sequence attached to the 5' end of the individual sequence-specific primers listed in FIG. 1.

Oligonucleotide primers were synthesized by Operon Technologies (Alameda, Calif.). Oligonucleotides were HPLC purified and quantitated by spectrophotometry.

EXAMPLE 2

DNA Preparation:

Whole blood samples were collected in high glucose ACD Vacutainers™ (Beckton Dickenson & Co., Franklin Lanes, N.J.). Following centrifugation, the buffy coat was collected and lysed with two washes of a 10:1 (v/v) solution of 14 mM NH$_4$Cl and 1 mM NaHCO$_3$. The lymphocytes were harvested by centrifugation, resuspended in lysis buffer (10 mM Tris-HCl, pH 8.0, 0.4 M NaCl, 2 mM EDTA, 0.5% SDS, 500 $\mu$g/ml proteinase K) and incubated overnight at 37° C. Samples were then extracted with ¼th volume of saturated NaCl, and the DNA was collected by ethanol precipitation. The final DNA pellet was washed with 70% ethanol, air dried and dissolved in TE (10 mM Tris-HCl, pH 7.5, 1 mM EDTA).

Buccal cell samples were obtained by brushing the lining of the buccal cavity for 30 seconds with a sterile cytology brush (Scientific Products #S7766-1a). DNA was prepared by immersing the brushes in 600 $\mu$l of 50 mM NaOH in 1.2 ml 96-well polypropylene tubes (USA/Scientific Plastics, Ocala, Fla.) and vortexed. The tubes, still containing the brushes, were heated to 95° C. for 5 min. and the brushes were carefully removed. The lysates were neutralized with 60 $\mu$l of 1 M Tris-HCl (pH 8.0) and vortexed. Samples were stored at 4° C.

EXAMPLE 3

Amplification Reaction:

Single amplifications were performed using 4 $\mu$l (1–2$\mu$g) and 10 $\mu$l (5–50ng) of genomic DNA prepared (described above) from either blood or buccal cells, respectively. 50 $\mu$l reaction mixtures were carried out in 1X PCR buffer (10 mM Tris-HCl, pH 8.3, 50 mM KCl, 1.5 mM MgCl$_2$), 200 $\mu$M dNTPs, and 2.5 units Taq polymerase (Perkin-Elmer, Norwalk, Conn.).

Multiplex PCR reactions were carried in a volume of 100 $\mu$l under the same conditions, except that 10 units of Taq polymerase per reaction was used.

To demonstrate the use of tagged primers for multiplex PCR, the 32 primer pairs presented in FIG. 1A and 1B (SEQ ID NO:32 through SEQ ID NO:95). were employed either alone, or as chimeric primers containing a 20 nucleotide tag (GCGGTCCCAAAAGGGTCAGT)(SEQ ID NO:1) corresponding to the M13mpl8 universal primer sequence (UPS) at the 5' end. The T$_m$ for all of the chimeric primers was calculated to be greater than 72° C.

Primer concentrations ranged from 0.25 to 1.0 $\mu$M. Amplifications were carried out using a Perkin-Elmer 9600 themocycler (Perkin-Elmer, Norwalk, Conn.) for 28 cycles with ramping (melting at 94° C. for 10s , annealing at 50° C., 55° C., 60° C., or 65° C. for 10 s, and extension at 72° C. for 10s)

After completion of the reaction, 8 $\mu$l of the reaction products were loaded directly onto a 2% ethidium bromide-stained agarose gel and subjected to electrophoresis at 250 volts for 90 minutes. The amplification products were visualized with a UV transilluminator and photographed with an Alpha Innotech IS-500 Digital Imaging System version 1.97 (Sun BIO Science, Inc., Branford, Conn.).

The following experiments were performed to demonstrate the effects on amplification of incorporating invention primer sequences into PCR primers.

EXAMPLE 4

Effect of Chimeric Primers on Efficiency and Specificity of Amplification

Three sequence-specific primer pairs used to amplify Exon 21 of the cystic fibrosis transmembrane regulator (CFTR) gene (Kerem et al., *Science* 245:1073, 1989) are shown in FIG. 2. A chimeric version of one of the three primers was synthesized containing the M13 UPS sequence 5'-GCGGTCCCAAAAGGGTCAGT-3' (SEQ ID NO:1)

immediately 5' to the illustrated sequences. The oligonucleotides were synthesized using conventional chemistry and were purified by high-performance liquid chromatography prior to use.

Primers were serially diluted two-fold for each primer pair (SS#1 (SEQ ID NO:62), SS#2 (SEQ ID NO:64), SS#3 (SEQ ID NO:66), and SS#3 (SEQ ID NO:66)+UPS (SEQ ID NO:1). See FIG. 1B). Primer pairs SS#1 (SEQ ID NO:62), SS#2 (SEQ ID NO:64), and SS#3 (SEQ ID NO:66) are sequence specific primers only; SS#3 (SEQ ID NO:66)+ UPS (SEQ ID NO:1) is chimeric with the 5' UPS (SEQ ID NO:1) sequence.

The results show that the addition of the UPS tag confers enhanced specificity over a four fold range of primer concentrations while retaining amplification efficiency at annealing temperatures from 50° to 65° C. Based on this and similar analyses of additional chimeric primer pairs, an annealing temperature of 60° C. was determined to be optimal for PCR amplification using UPS-tagged primers.

The efficiencies with which the three CFTR primer pairs (designated SS#1 (SEQ ID NO:62), SS#2 (SEQ ID NO:64), and SS#3 (SEQ ID NO:66) primed amplification varied with primer concentration and temperature of annealing (FIGS. 2A through 2D). The primer concentrations were as follows: Lanes 1, 4, 7, and 10, (1.0 μM); lanes 2, 5, 8, and 11, (0.5 μM); and lanes 3, 6, 9, and 12, (0.25 μM). The temperatures of annealing were 50° C., 55° C., 60° C. and 65° C., as indicated.

The SS#1 (SEQ ID NO:62) and SS#3 (SEQ ID NO:66) primers, for example, were noticeably inefficient at annealing temperatures above 60° C. The primer pair designated SS#3 (SEQ ID NO:66)-UPS, which corresponds to the SS#3 (SEQ ID NO:66) primers having the M13 UPS (SEQ ID NO:64) sequence on their 5' termini, was highly efficient in priming at all temperatures tested; furthermore, few spurious amplification products were detected in reactions containing SS#3 (SEQ ID NO:66)-UPS primers. By contrast, SS#2 (SEQ ID NO:64) primers gave spurious amplification products at all three temperatures below 65° C.

EXAMPLE 5

Multiplex Amplification with Chimeric Primers

To assess the use of chimeric primers for multiplex PCR, a system was designed using 15 UPS-tagged primer pairs specific for the cystic fibrosis transmembrane conductance regulator locus (CFTR). An example of the gel electrophoretic pattern of the multiplex PCR products is shown in FIG. 3.

As demonstrated for exon 21 (FIGS. 2A through 2D), each chimeric primer pair concentration used within the CFTR 15-plex was determined by performing independent amplicon amplifications over a range of concentrations. Lanes 1–3; multiplex amplification of 3 different genomic DNA samples isolated from blood. All samples were amplified with CFTR chimeric 15-plex primers (See FIG. 1A) at the following primer pair concentrations: Int 19; 0.5 μM. exon 19; 0.5 μM. exon 21; 1.0 μM. exon 9; 0.75 μM. exon 13; 1.0 μM. exon 4; 1.0 μM. exon 17b; 0.5 μM. exon 7; 0.5 μM. exon 11; 1.0 μM. exon 10; 1.0 μM. exon 20; 0.25 μM. exon 5; 0.5 μM. exon 14 b; 0.5 μM. exon 12; 0.5 μM. exon 3; 0.25 μM. Lane M; ΦX174 Hae III digested marker DNA.

Using the same amplification conditions that were originally defined for the individual chimeric primer pairs, all 15 of the predicted CFTR PCR products co-amplified with relative ease. It should be emphasized that the CFTR multiplex reactions presented in FIG. 3 and all subsequent reactions employed the same reaction components, cycling times and temperatures without modification from the single amplicon assay conditions. The only optimization required was an adjustment of the primer concentrations for intron 19 and exon 19 to generate comparable band intensities of the co-amplified products.

EXAMPLE 6

Comparison of Multiplex PCR Reactions Using CFTR Primer Pairs Lacking and Containing M13 UPS (SEQ ID NO:1).

To demonstrate the enhanced specificity and efficiency conferred by the UPS (SEQ ID NO:1) sequence in multiplex PCR, parallel reactions were carried out using UPS (SEQ ID NO:1)-tagged CFTR primers and the corresponding non-tagged primers. Identical reaction conditions, cycling times and primer concentrations were used for both primer sets. Previously, optimal primer concentrations were determined for the individual primer pairs. Coincidentally, the optimal concentrations determined in this manner were identical for both the UPS (SEQ ID NO:1) and non-UPS (SEQ ID NO:1) tagged primers.

Figure 4:
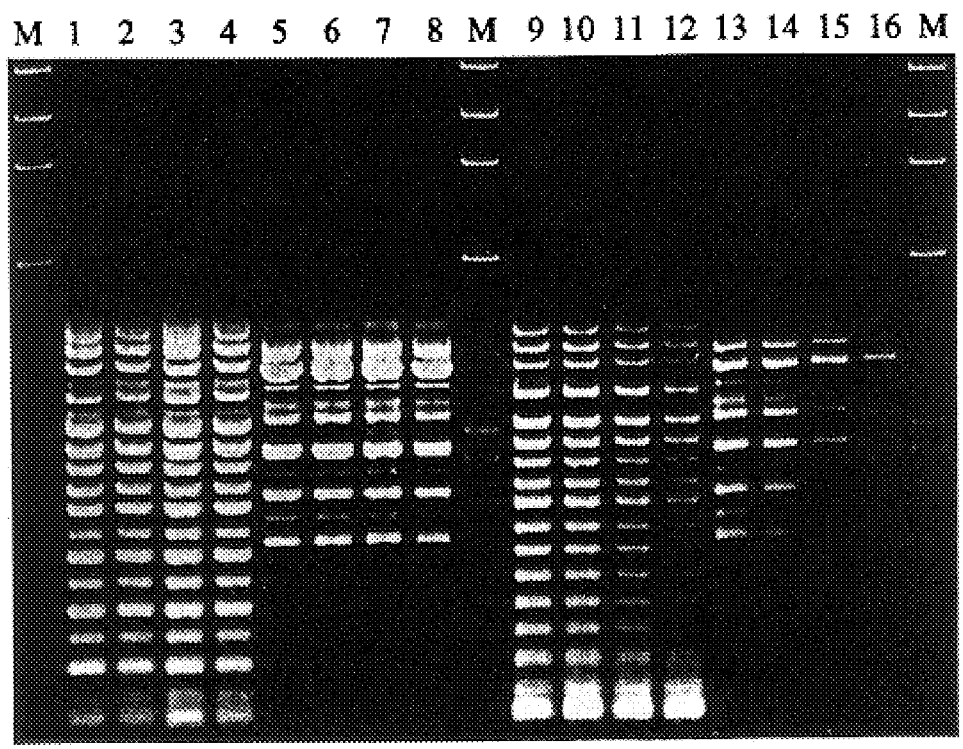
FIG. 4 shows gel comparison of chimeric primers with sequence-specific primers for CFTR 15-plex PCR amplification.

FIG. 4 shows the results of agarose gel comparison of chimeric primers with sequence-specific primers for CFTR 15-plex PCR amplification. Lanes 1–8; genomic DNA samples isolated from blood. Lanes 9–16; genomic DNA samples isolated from buccal cells. Each consecutive sample in the group of four amplifications represents a two-fold serial dilution of genomic DNA. Lanes 1–4 and 9–12; CFTR 15-plex amplification with chimeric primers. Lanes 5–8 and 13–16; CFTR 15-plex amplification with sequence-specific primers. Lane M; ΦX174 Hae III digested marker DNA.

As shown, the multiplex amplification using the standard sequence-specific primer pairs failed to generate a clear multiplex PCR profile of the CFTR locus. Specifically, several of the expected bands were clearly under-represented, presumably due to differential PCR amplification of their respective products (FIG. 4, lanes 5–8 and lanes 13–16).

In contrast, a clear multiplex profile was obtained when the CFTR locus was amplified with the corresponding UPS (SEQ ID NO:1)-tagged primer pairs. The expected bands were clearly prominent and virtually free of contaminating products (FIG. 4, lanes 1–4 and 9–12). Moreover, equivalent banding patterns were observed over an 8-fold range of template concentrations when UPS (SEQ ID NO:1)-tagged primer pairs were employed.

Conversely, the amplification profile generated using sequence-specific primers was sensitive to variations in the template concentration as evident by the changes in the intensity of individual bands (FIG. 4, lanes 5–8 and 13–16).

EXAMPLE 7

Use of Multiplex PCR to Simultaneously Amplify Different Disease-related Sequences Under Identical Conditions To further demonstrate the general utility of the UPS (SEQ ID NO:1)-tagged primers, 64 different human genomic target sequences (FIGS. 1A and 1B) were amplified in a single thermal cycler under identical reaction conditions and cycling parameters. Results from these amplification reactions using sequence-specific primer pairs and the cognate UPS (SEQ ID NO:1)-tagged primer pairs are presented in FIG. 5 and FIG. 6.

Figure 5:
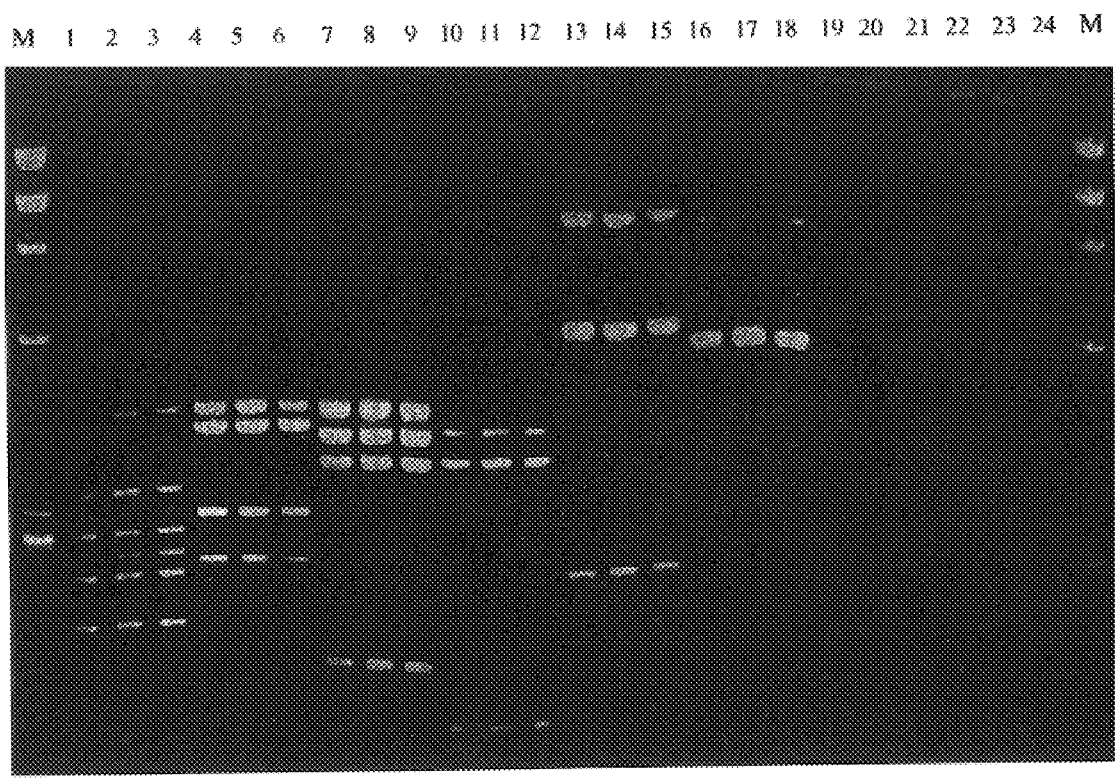
FIG. 5 shows the results from multiple gene loci amplifications performed in a single PCR thermal cycler under identical reaction conditions and cycling parameters.

The banding patterns for the following primer sets are displayed in FIG. 5: lanes 1–3 amplification of CFTR 15-plex with chimeric primers; lanes 4–6 amplification of CFTR 15-plex with sequence-specific primers; lanes 7–9 multiplex amplification of α-galactosidase Gaucher's disease (GCR)(Kornreich et al., *Nuc. Acids Res.* 17:3301, 1989) 3-plex and single Sickle Cell Anemia (SCA)(Navon et al., Science 243:1471, 1989) target with chimeric primers; lanes 10–12 multiplex amplification of GCR 3-plex and single SCA target with sequence specific primers; lanes 13–15 multiplex amplification of single GCR target and Tay-Sachs (TS) (Tanaka et al., *Am. J. Hum. Genet.* 46:329, 1990) 2-plex with chimeric primers; lanes 16–18 multiplex amplification of single GCR target and TS 2-plex with sequence-specific primers; lanes 19–21 amplification of single β-thalassemia target with chimeric primers; and lanes 22–24 amplification of single β-thalassemia target with sequence-specific primers. Lane M; ΦX174 Hae III digested marker DNA. All primer pairs were tested on 3 different genomic DNA samples isolated from: lanes 1–8 genomic DNA samples isolated from blood cells, while in lanes 9–12 the genomic DNA template was derived from buccal cells.

Figure 6:
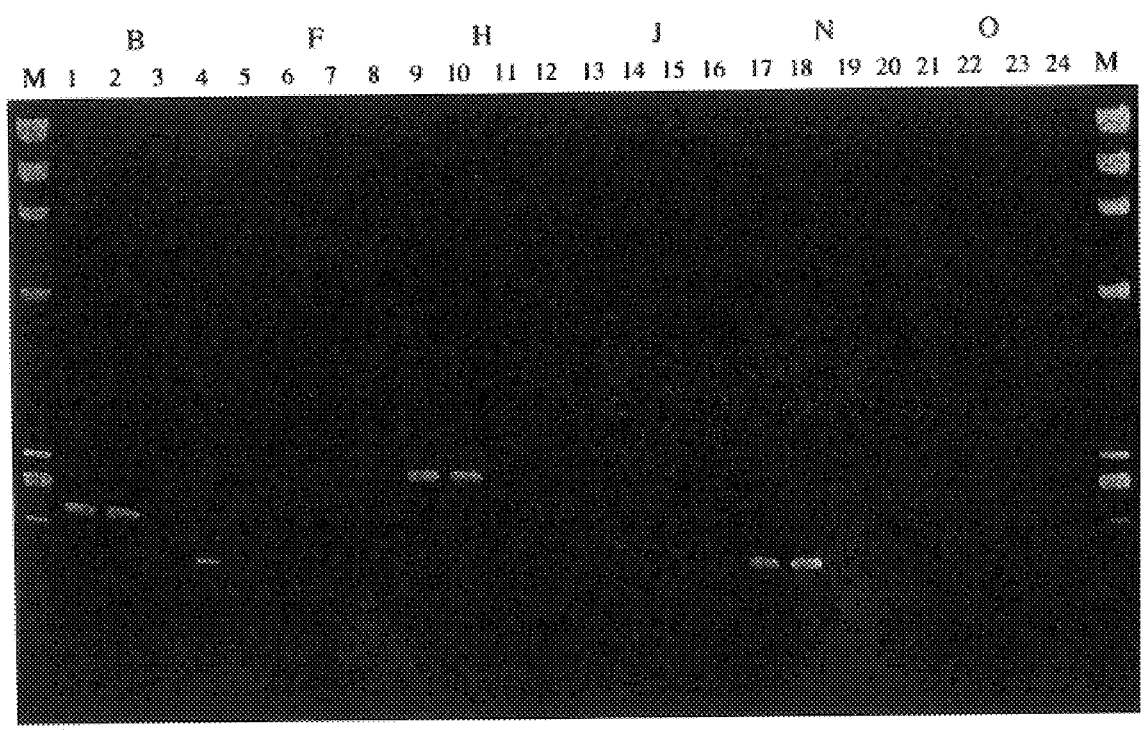
FIG. 6 shows the results from multiple gene loci amplifications performed in a single PCR thermal cycler under identical reaction conditions and cycling parameters.

FIG. 6 shows the results of independent amplification of six target sequences within the human Wilms Tumor gene (WT1) (Varanasi et al., *Proc. Natl. Acad.Sci.USA* 91:3554, 1994). Lanes 1, 2, 5, 6, 9, 10, 13, 14, 17, 18, 21 and 22; amplifications performed with chimeric primers. Lanes 3, 4, 7, 8, 11, 12, 15, 16, 19, 20, 23 and 24; amplifications performed with sequence-specific primers. Amplifications represent each of six amplicons within the WT-1 gene (B, F, II, J, N, and O; see FIG. 1). All primer pairs tested on two independent genomic DNA samples isolated from blood. Lane M; ΦX174 Hae III digested marker DNA. With the exception of one primer pair (FIG. 6, lanes 5–8) which did not generate a detectable product when the chimeric primer was employed, the presence of the UPS (SEQ ID NO:1) sequence enhanced the yield of the respective PCR products (FIG. 6, lanes 1–4, 9–12, 13–16, 17–20, 21–24).

Results from the multiplex PCR reactions presented herein demonstrate that for both single gene multiplexes (FIG. 5, lanes 1–3) and multiplex reactions involving more than one gene (FIG. 5, lanes 7–9, 13–15), the UPS (SEQ ID NO:1)-tagged primers generated only the desired bands, and the co-amplified products were more uniform with respect to the band intensities than the corresponding products generated from the non-tagged sequence-specific primers (FIG. 6, lanes 4–6, 10–12, 16–18).

What is claimed is:

1. A multiplicity of single-stranded oligonucleotide DNA primers for simultaneous amplification of multiple target DNA sequences under a single set of reaction conditions in a multiplex polymerase chain reaction (PCR), said primers having a 5'X domain and a 3' Y domain, wherein
   a) each said 5' X domain comprises a sequence that does not hybridize to said multiple target sequences;
   b) the melting temperature of a hybrid between X and its complement in the absence of other sequences is greater than about 60° C.; and
   c) Y comprises a sequence contained within or flanking said target sequence or its complement
   d) each of said primers being capable of annealing specifically with it cognate target sequence under uniform high stringency annealing conditions during said amplification.

2. The primer of claim 1, wherein X comprises the sequence 5'-GCGGTCCCAAAAGGGTCAGT-3' (SEQ ID NO:1).

3. The primer of claim 1, wherein X comprises the sequence 5'-CGCCAGGGTTTTCCCAGTCA-3' (SEQ ID NO:2).

4. The primer of claim 1, wherein X comprises the sequence 5'-CGCCAGGGGGGGCCCAGTCA-3' (SEQ ID NO:3).

5. The primer of claim 1, wherein X comprises the sequence 5'-CGGCAGCGGGGCCCAGTCCA-3' (SEQ ID NO:4).

6. The primer of claim 1, wherein X comprises the sequence 5'-CGCGGCCGGGGCCCATCCCA-3' (SEQ ID NO:5).

7. The primer of claim 1, wherein X comprises the sequence 5'-CGCGGCCGGGGCCATCTCAA-3' (SEQ ID NO:6).

8. The primer of claim 1, wherein X comprises the sequence 5'-GAGGCCGGTGGCCATGTCAA-3' (SEQ ID NO:7).

9. The primer of claim 1, wherein X comprises the sequence 5'-TAGGCGCGTGGCCATGTCAA-3' (SEQ ID NO:8).

10. The primer of claim 1, wherein X comprises the sequence 5'-TAGGCCCGTGGCCATGTTAA-3' (SEQ ID NO:9).

11. The primer of claim 1, wherein X comprises the sequence 5'-TAGGCCCGTGGCAATATTAA-3' (SEQ ID NO:10).

12. The primer of claim 1, wherein X comprises the sequence 5'-CCGGTCCGTGGCAATATTAA-3' (SEQ ID NO:11).

13. The primer of claim 1, wherein X comprises the sequence 5'-CCGGCTCGTGGCGATGTTAA-3' (SEQ ID NO:12).

14. The primer of claim 1, wherein X comprises the sequence 5'-CCGGCGTGTGCCGATATTAA-3' (SEQ ID NO:13).

15. The primer of claim 1, wherein X comprises the sequence 5'-CCATGCGTGTGCCGATATTA-3' (SEQ ID NO:14).

16. The primer of claim 1, wherein X comprises the sequence 5'-CAATGCGGGCGCCGATATTA-3' (SEQ ID NO:15).

17. The primer of claim 1, wherein X comprises the sequence 5'-CGATGCGGGAGCCAATATAA-3' (SEQ ID NO:16).

18. The primer of claim 1, wherein X comprises the sequence 5'-AGATGCGGTAGCCAATATAA-3' (SEQ ID NO:17).

19. The primer of claim 1, wherein X comprises the sequence 5'-GGCGTGCTGAGCCAATATGG-3' (SEQ ID NO:18).

20. The primer of claim 1, wherein X comprises the sequence 5'-GGCGCGCTGAGCCAATATGG-3' (SEQ ID NO:19).

21. The primer of claim 1, wherein X comprises the sequence: 5'-GGCGCGCCGAGCCAATATGG-3' (SEQ ID NO:20).

22. The primer of claim 1, wherein X comprises the sequence 5'-GGCGCGCCGAGCTAATATAT-3' (SEQ ID NO:21).

23. The primer of claim 1, wherein X comprises the sequence 5'-AGCTCGGCGAGCTAATATAT-3' (SEQ ID NO:22).

24. The primer of claim 1, wherein X comprises the sequence 5'-AGCGCGGCCAGCTAAGAGAT-3' (SEQ ID NO:23).

25. The primer of claim 1, wherein X comprises the sequence 5'-CGCGCGGCCGGCTGGAGAGA-3' (SEQ ID NO:24).

26. The primer of claim 1, wherein X comprises the sequence 5'-CGCGAGGCCGGCTGTAGAGG-3' (SEQ ID NO:25).

27. The primer of claim 1, wherein X comprises the sequence 5'-CGCGAGGCCAGCGGCCGAGG-3' (SEQ ID NO:26).

28. The primer of claim 1, wherein X comprises the sequence 5'-CGCGAGGCCAGCGGTCGAGG-3' (SEQ ID NO:27).

29. The primer of claim 1, wherein X comprises the sequence 5'-CGCGAGGCCAGCGGTCGAGG-3' (SEQ ID NO:28).

30. The primer of claim 1, wherein X comprises the sequence 5'-CGCGGGGCCCGCGGCCGCGG-3' (SEQ ID NO:29).

31. The primer of claim 1, wherein X comprises the sequence 5'-CGCCCGCCGCGCCCCGCGCC-3' (SEQ ID NO:30).

32. The primer of claim 1, wherein X comprises the sequence 5'-GGCGCTCCATTAGCGTGAGT-3' (SEQ ID NO:31).

33. The primer of claim 1, wherein X and Y each comprise from 17 to 20 bases.

34. The primer of claim 1, wherein the melting temperature of a hybrid formed between said primer and its complement in a solution of 0.5 M NaCl is at least 72° C.

* * * * *